US006830751B1

(12) United States Patent
Leonard et al.

(10) Patent No.: US 6,830,751 B1
(45) Date of Patent: Dec. 14, 2004

(54) USE OF IL-12 ANTAGONISTS IN THE TREATMENT OF RHEUMATOID ARTHRITIS

(75) Inventors: John Leonard, Manchester, NH (US); Samuel Goldman, Acton, MA (US); Richard O'Hara, Jr., Quincy, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 09/512,701

(22) Filed: Feb. 25, 2000

Related U.S. Application Data

(62) Division of application No. 08/560,943, filed on Nov. 20, 1995, now abandoned, which is a continuation of application No. 08/212,629, filed on Mar. 14, 1994, now abandoned.

(51) Int. Cl.[7] ...................... A61K 39/395; A61K 38/00; A61K 38/21; A01N 37/18; C12P 21/08

(52) U.S. Cl. ................ 424/130.1; 424/85.4; 424/134.1; 424/141.1; 424/178.1; 530/388.1; 530/387.1; 530/388.23; 514/2

(58) Field of Search .......................... 424/130.1, 141.1, 424/85.4, 178.1, 134.1; 530/388.1, 387.1, 388.23; 514/2

(56) References Cited

U.S. PATENT DOCUMENTS

| | | | |
|---|---|---|---|
| 5,536,657 A | 7/1996 | Chua et al. | |
| 5,547,852 A | 8/1996 | Seiler et al. | |
| 5,650,492 A | 7/1997 | Gately et al. | |
| 5,840,530 A | 11/1998 | Gubler et al. | |
| 5,852,176 A | 12/1998 | Gubler et al. | |
| 5,853,721 A | 12/1998 | Gately et al. | |
| 5,955,476 A | 9/1999 | Muller et al. | |
| 5,969,102 A | 10/1999 | Bram et al. | |
| 6,054,487 A | 4/2000 | Sekut et al. | |
| 6,225,117 B1 | 5/2001 | Gately et al. | |
| 6,258,562 B1 | 7/2001 | Salfeld et al. | |
| 6,338,848 B1 * | 1/2002 | Leonard et al. ......... | 424/130.1 |
| 6,469,017 B1 * | 10/2002 | Klaus et al. | |

FOREIGN PATENT DOCUMENTS

| | | | |
|---|---|---|---|
| CA | 2123049 | 11/1994 | |
| DE | 43 15 127.2 | 11/1993 | .......... A61K/37/02 |
| EP | 0 433 827 A2 | 6/1991 | |
| EP | 0 625 354 A1 | 11/1994 | |
| EP | 0 638 644 A1 | 2/1995 | |
| EP | 0 640 689 A2 | 3/1995 | |
| WO | WO 93/19770 | 10/1993 | |
| WO | WO 98/16248 | 4/1998 | |
| WO | WO98/22137 | * 5/1998 | |
| WO | WO 98/41232 | 9/1998 | |
| WO | WO 99/37682 | 7/1999 | |

OTHER PUBLICATIONS

Hess et al, Eur. J. Immunol. 26:187–191, 1996.*
Croonian Lecture 1995 J. Royal College of Physicans of London 30/4:344–351, Aug. 1996.*
Neurath et al, J. Exp. Medicine 182:1281–90, Nov. 1995.*
Trembleau et al Immunology Today 16/8:383–386, 1995.*
Wysocka et al, Eur. J. Immunol. 25:672–76, 1995.*
Ozmen et al, J. Exp. Med. 180:907–915, Sep. 1994.*
Germann et al, PNAS, USA, 92:4823–27, May 1995.*
Verhoeven et al, British Society for Rheumatology 37:612–619, 1996.*
Gubler et al, PNAS, USA; 88:4143–4147, 1991.*
Kim et al, Clin. Exp. Immunol., 119:175–181, 2000.*
Trembleau et al, J. Exp. Med. 181:817–21, Feb. 1995.*
Borigini et al Bailliere's Clinical Rheumatology 9/4:689–710, Nov. 1995.*
Amaudova et al., Application of Interferon–γ Containing Gel for Local Treatment of Skin Ulcers in Autoimmune Vasculitides and Skin Changes in Progressive Systemic Sclerosis, *The Journal of Rheumatology*, 20:1445–1446 (1993).
Bach, Immunosuppressive Therapy of Autoimmune Diseases, *Immunology Today*, 14:322–326 (1993).
Bach, Immunosuppressive Therapy of Autoimmune Diseases, *Trends in Pharmacological Sciences*, 14:213–216 (1993).
Balashov et al., Increased Interleukin 12 Production in Progressive Multiple Sclerosis: Induction by Activated CD4[+] T Cells Via CD40 Ligand, *Proceedings of the National Academy of Sciences U.S.A.*, 94:599–603 (1997).
Bankhurst, Interferons and Systemic Lupus Erythematosus, *Journal of Rheumatology*, 14:63–67 (1987).
Baron et al., Production of Tumor Necrosis Factor and Other Proinflammatory Cytokines by Human Mononuclear Phagocytes Stimulated with Myelin P2 Protein, *Proceedings of the National Academy of Sciences U.S.A.*, 90,4414–4418 (1993).
Baron et al., Surface Expression of α4 Integrin by CD4 T Cells is Required for Their Entry into Brain Parenchyma, *Journal of Experimental Medicine*, 177:57–68 (1993).
Butler et al., Anti–IL–12 and Anti–TNF Antibodies Synergistically Suppress the Progression of Murine Collagen–Induced Arthritis, *European Journal of Immunology*, 29:2205–2212 (1999).

(List continued on next page.)

Primary Examiner—N. M. Minnifield
(74) Attorney, Agent, or Firm—Finnegan, Henderson, Farabow, Garrett & Dunner, L.L.P.

(57) ABSTRACT

Method of treating autoimmune conditions are disclosed comprising administering to a mammalian subject IL-12 or an IL-12 antagonist. In certain preferred embodiments the autoimmune condition is one which is promoted by an increase in levels of IFN-γ or TNF-α. Suitable conditions for treatment include multiple sclerosis, systemic lupus erythematosus, rheumatoid arthritis, autoimmune pulmonary inflammation, Guillain-Barre syndrome, autoimmune thyroiditis, insulin dependent diabetes melitis and autoimmune inflammatory eye disease.

13 Claims, 6 Drawing Sheets

OTHER PUBLICATIONS

Campbell et al., Essential Role for Interferon–γ and Interleukin–6 in Autoimmune Insulin–Dependent Diabetes in NOD/Wehi Mice, *Journal of Clinical Investigation*, 87:739–742 (1991).

Castaño et al., Type–I Diabetes: A Chronic Autoimmune Disease of Human, Mouse, and Rat, *Annual Review of Immunology*, 8:647–679 (1990).

Chan et al., Induction of Interferon γ Production by Natural Killer Cell Stimulatory Factor: Characterization of the Responder Cells and Synergy with Other Inducers, *Journal of Experimental Medicine*, 173:869–879 (1991).

Charteris et al., Interferon–Gamma (IFN–γ) Production In Vivo in Experimental Autoimmune Uveoretinitis, *Immunology*, 75:463–467 (1992).

Chizzonite et al., IL–12 Receptor. I. Characterization of the Receptor on Phytohemagglutinin–Activated Human Lymphoblasts, *The Journal of Immunology*, 148:3117–3124 (1992).

Chizzonite et al., IL–12: Monoclonal Antibodies Specific for the 40–kDa Subunit Block Receptor Binding and Biologic Activity on Activated Human Lymphoblasts, *The Journal Immunology*, 147:1548–1556 (1991).

Chofflon et al., Tumor Necrosis Factor α Production as a Possible Predictor of Relapse in Patients with Multiple Sclerosis, *European Cytokine Network*, 3:523–531 (1992).

Chua et al., Expression Cloning of a Human IL–12 Receptor Component: A New Member of the Cytokine Receptor Superfamily with Strong Homology to gp 130, *The Journal of Immunology*, 153:128–136 (1994).

Constantinescu et al., IL–12 Reverses the Suppressive Effect of the CD40 Ligand Blockade on Experimental Autoimmune Encephalomyelitis (EAE), *Journal of the Neurological Sciences*, 171:60–64 (1999).

Deguchi et al., Tumour Necrosis Factor/Cachectin Plays a Key Role in Autoimmune Pulmonary Inflammation in Lupus–Prone Mice, *Clinical and Experimental Immunology*, 85:392–395 (1991).

Duchmann et al., Interleukin–12 mRNA is Induced in Lamina Propria Mononuclear Cells from Patients with Inflammatory Bowel Disease (IBD), *Gastroenterology (Suppl.)*, 104:A693 (1993).

Feldmann et al., Evaluation of the Role of Cytokines in Autoimmune Disease: The Importance of TNFα in Rheumatoid Arthritis, *Progress in Growth Factor Research*, 4:247–255 (1992).

Fox et al., Anti–Interleukin–12 Antibody: Potential Role in Preventing Relapses of Multiple Sclerosis, *BioDrugs*, 13:233–241 (2000).

Fujihira et al., Suppression and Acceleration Diabetes by Neutralization of Endogenous Interleukin–12 in NOD Mice, *Diabetes*, 49:1998–2006 (2000).

Funauchi et al., Serum Level of Interferon–γ in Autoimmune Diseases, *Tohoku Journal of Experimental Medicine*, 164:259–267 (1991).

Gately et al., Interleukin–12 Antagonist Activity of Mouse Interleukin–12 p40 Homodimer in Vitro and in Vivo, *Annals New York Academy of Sciences*, 795:1–12 (1996).

Germann et al., IL–12, a Cytokine with Multiple Effects on $T_H1-$, but not on $T_H2-$cells, *Immunobiology*, 186:38 (1992).

Godfrey et al., A Developmental Pathway Involving Four Phenotypically and Functionally Distinct Subsets of $CD3^-CD4^-CD8^-$ Triple–Negative Adult Mouse Thymocytes Defined by CD44 and CD25 Expression, *The Journal of Immunology*, 150:4244–4252 (1993).

Greig et al., A Comparison of the Effects of Melengestrol Acetate and Hydrocortisone Acetate on Experimental Allergic Encephalomyelitis in Rats, *The Journal of Pharmacology and Experimental Therapeutics*, 173:85–93 (1970).

Harris, et al., Therapeutic Antibodies—The Coming of Age, *Trends in Biotechnology*, 11:42–44 (1993).

Heremans et al., Role of Endogenous Interleukin–12 (IL–12) in Induced and Spontaneous Relapses of Experimental Autoimmune Encephalomyelitis in Mice, *European Cytokine Network*, 10:171–179 (1999).

Higgins et al., Suppression of Experimental Autoimmune Encephalomyelitis by Oral Administration of Myèlin Basic Protein and Its Fragments, *The Journal of Immunology*, 140:440–445 (1988).

Hofman et al., Immunoregulatory Molecules and IL 2 Receptors Identified in Multiple Sclerosis Brain, *The Journal of Immunology*, 136:3239–3245 (1986).

Hofman et al., Lymphokines and Immunoregulatory Molecules in Subacute Sclerosing Panencephalitis, *Clinical Immunology and Immunopathology*, 58:331–342 (1991).

Hofman et al., Tumor Necrosis Factor Identified in Multiple Sclerosis Brain, *Journal of Experimental Medicine*, 170:607–612 (1989).

Hunter et al., Immunoregulation by Interleukin–12 in MB49.1 Tumor–Bearing Mice: Cellular and Cytokine–Mediated Effector Mechanisms, *European Journal of Immunology*, 27:3438–3446 (1997).

Ichikawa et al., Anti–IL–12 Antibody Prevents the Development and Progression of Multiple Sclerosis–Like Relapsing–Remitting Demyelinating Disease in NOD Mice Induced with Myelin Oligodendrocyte Glycoprotein Peptide, *Journal of Neuroimmunology*, 102:56–66 (2000).

Jaffe, Combination Therapy of Rheumatoid Arthritis—Rationale and Overview, *Journal of Rheumatology*, 17 (supplement 25):24–27 (1990).

Joosten et al., Blockade of endogenous interleukin 12 results in suppression of murine streptococcal cell wall arthritis by enhancement of interleukin 10 and interleukin 1Ra, *Annals of Rheumatic Diseases*, 59(3): 196–205 (2000).

Karlsson et al., Autoimmune Endocrinopathies 5: Autoimmune Disease of the Adrenal Cortex, Pituitary, Parathyroid Glands and Gastric Mucosa, *Journal of Internal Medicine*, 234:379–386 (1993).

Kim et al., The role of IL–12 in Inflammatory Activity of Patients with Rheumatoid Arthritis (RA), *Clinical and Experimental Immunology*, 119:175–181 (2000).

Kobayashi et al., Identification and Purification of Natural Killer Cell Stimulatory Factor (NKSF), a Cytokine with Multiple Biologic Effects on Human Lymphocytes, *Journal of Experimental Medicine*, 170:827–845 (1989).

Lagoo et al., Proinflammatory Cytokine Production by Rheumatoid Arthritis Synovial Fibroblasts, *Journal of Cellular Biochemistry (Suppl. O)*, 17:146 (1993).

Leonard et al., Effects of Single–Dose Interleukin–12 Exposure on Interleukin–12–Associated Toxicity and Interferon–γ Production, *Blood*, 90:2541–2548 (1997).

Leonard et al., Prevention of Experimental Autoimmune Encephalomyelits by Antibodies Against Interleukin 12, *Journal of Experimental Medicine*, 181:381–386 (1995).

Leonard et al., Regulation of Experimental Autoimmune Encephalomyelitis by Interleukin–12, *Annals New York Academy of Sciences*, 795:216–226 (1996).

Leonard et al., Regulation of the Inflammatory Response in Animal Models of Multiple Sclerosis by Interleukin–12, *Critical Reviews in Immunology*, 17:545–553 (1997).

Lernmark et al., Autoimmune Endocrinopathies 3: Islet Cell Autoimmunity, *Journal of Internal Medicine*, 234:361–369 (1993).

Malfait et al., Blockade of IL–12 During the Induction of Collagen–Induced Arthritis (CIA) Markedly Attenuates the Severity of the Arthritis, *Clinical and Experimental Immunology*, 111:377–383 (1998).

Manetti et al., Natural Killer Cell Stimulatory Factor (Interleukin 12 [IL–12]) Induces T Helper Type 1 (Th1)–Specific Immune Responses and Inhibits the Development of IL–4–Producing Th Cells., *Journal of Experimental Medicine*, 177:1199–1204 (1993).

Merrill et al., Inflammatory Leukocytes and Cytokines in the Peptide–Induced Disease of Experimental Allergic Encephalomyelitis in SJL and B10.PL Mice, *Proceedings of the National Academy of Sciences U.S.A.*, 89:574–578 (1992).

Merrill et al., T Cell Lines Established from Multiple Sclerosis Cerebrospinal Fluid T cells Using Human Retroviruses, *Journal of Neuroimmunology*, 21:213–226 (1989).

Panitch et al., Treatment of Multiple Sclerosis with Gamma Interferon: Exacerbations Associated with Activation of the Immune System, *Neurology*, 37:1097–1102 (1987).

Peeva et al., Rheumatoid Arthritis Exacerbation Caused by Exogenous Interleukin–12, *Arthritis & Rheumatism*, 43:461–463 (2000).

Rothe et al., Suppression of Cyclophosphamide Induced Diabetes Development and Pancreatic Th1 Reactivity in NOD Mice Treated with the Interleukin (IL)–12 Antagonist IL–12(p40)$_2$, *Diabetologia*, 40:641–646 (1997).

Saito et al., Effect of CD80 and CD86 Biockade and Anti–Interleukin–12 Treatment on Mouse Acute Graft–Versus–Host Disease, *European Journal of Immunology*, 26:3098–3106 (1996).

Serreze, Autoimmune diabetes results from genetic defects manifest by antigen presenting cells, *FASEB Journal*, 7:1092–1096 (1993).

Simon et al., Divergent T–cell Cytokine Patterns in Inflammatory Arthritis, *Proceedings of the National Academy of Sciences U.S.A.*, 91:8562–8566 (1994).

Smith et al., Interleukin–12 Induces Relapse in Experimental Allergic Encephalomyelitis in the Lewis Rat, *American Journal of Pathology*, 150:1909–1917 (1997).

Smith et al., The Role of T Cells in Myosin–Induced Autoimmune Myocarditis, *Clinical Immunology and Immunopathology*, 68:100–106 (1993).

Steinman, Autoimmune Disease: Misguided Assaults on the Self Produce Multiple Sclerosis, Juvenile Diabetes and Other Chronic Illnesses: Promising Therapies are Emerging, *Scientific American*, Sep.: 107–114 (1993).

Tang, et al., The Effects of a Monoclonal Antibody to Interferon–γ on Experimental Autoimmune Thyroiditis (EAT): Prevention of Disease and Decrease of EAT–Specific T Cells, *European Journal of Immunology*, 23:275–278 (1993).

Trinchieri et al., Natural Killer Cell Stimulatory Factor (NKSF) or Interleukin–12 is a Key Regulator of Immune Response and Inflammation, *Progress in Growth Factor Research*, 4:355–368 (1992).

Van der Veen et al., The Effect of Methylprednisone Pulse Therapy on Methyltrexate Treatment of Rheumatoid Arthritis, *Clinical Rheumatology*, 12:500–505 (1993).

Veys et al., Interferon Gamma in Rheumatoid Arthritis—A Double Blind Study Comparing Human Recombinant Interferon Gamma with Placebo, *The Journal of Rheumatology*, 15:570–574 (1988).

Via et al., IL 12 Prevents Autoimmunity in a Murine Model of SLE., *Arthritis and Rheumatism*, 36:148 (1993).

Vitali, et al., Immunotherapy in Rheumatoid Arthritis, *The International Journal of Artificial Organs*, 16:196–200 (1993).

Waldburger et al., Adoptive Transfer of Experimental Allergic Encephalomyelitis After in Vitro Treatment with Recombinant Murine Interleukin–12, *American Journal of Pathology*, 148:375–382 (1996).

Wilske, Approaches to the Management of Rheumatoid Arthritis: Rationale for Early Combination Therapy, *British Journal of Rheumatology*, 32 (supplement 1) 24–27 (1993).

Kelso, et al., "Heterogeneity in Lymphokine Profiles of CD4+ and CD8+ T Cells and Clones Activated in vivo and in vitro" *Immunological Reviews*, 123:85–114 (1991).

Becher et al., "Experimental autoimmune encephalitis and inflammation in the absence of interleukin–12," *Jour. Clin. Invest.*, 110(4):493–497 (2002).

Benson et al., "The role of IL–23 in experimental autoimmune encephalomyelitis," *FASEB Journal*, 16(5):A1045 (2002).

Fuss et al., "Disparate CD4$^+$ lamina propria (LP) lumphokine secretion profiles in inflammatory bowel disease," *The Journal of Immunology*, 57(3):1261–1270 (1996).

Germann et al., "Administration of interleukin 12 in combination with type II collagen induces severe arthritis in DBA/1 mice," *Proc. Natl. Acad. Sci. USA*, 92:4823–4827 (1995).

Gran et al., "IL–12p35–deficient mice are susceptible to experimental autoimmune encephalomyelitis: evidence for redundancy in the IL–12 system in the induction of central nervous system autoimmune demyelination," *The Journal of Immunology*, 169(12):7104–7110 (2002).

Mattner et al., "The interleukin–12 subunit p40 specifically inhibits effects of the interleukin–12 heterodimer," *Eur. J. Immunol.*, 23:2202–2208 (1993).

Romagnani, S., "Human TH1 and TH2 subsets: regulation of differentiation and role in protection and immunopathology," *Int. Arch. Allergy Immunol.* 98:279–285 (1992).

Via et al., "IL–12 stimulates the development of acute graft–versus–host disease in mice that normally would develop chronic, autoimmune graft–versus–host disease," *The Journal of Immunology*, 153(9):4040–4047 (1994).

U.S. patent application Ser. No. 08/087,832, Gately et al., filed Jul. 2, 1993.

U.S. patent application Ser. No. 08/094,649, Chizzonite et al., filed Jul. 19, 1993.

U.S. patent application Ser. No. 08/094,713, Chua et al., filed Jul. 19, 1993.

\* cited by examiner

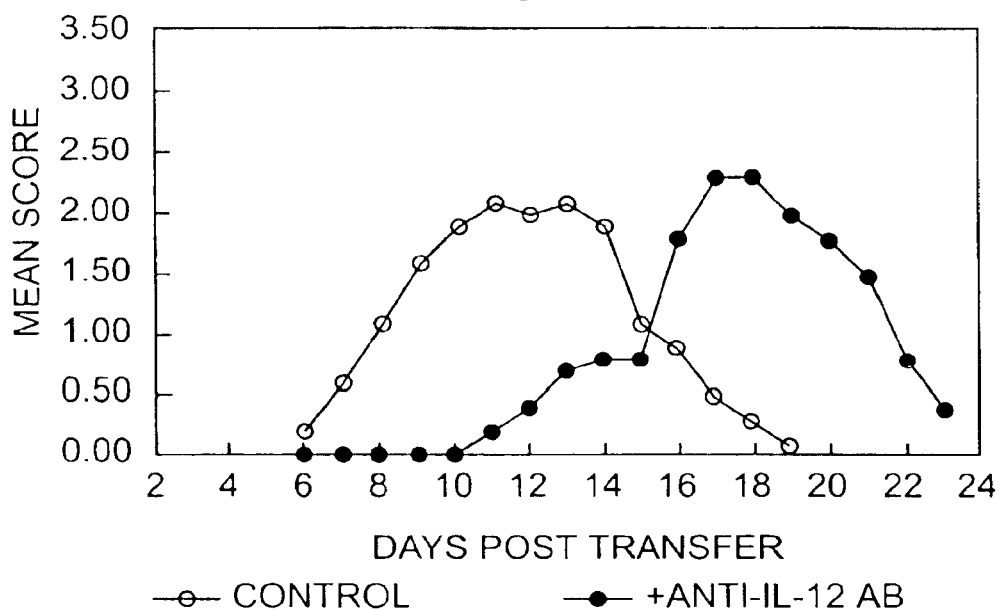
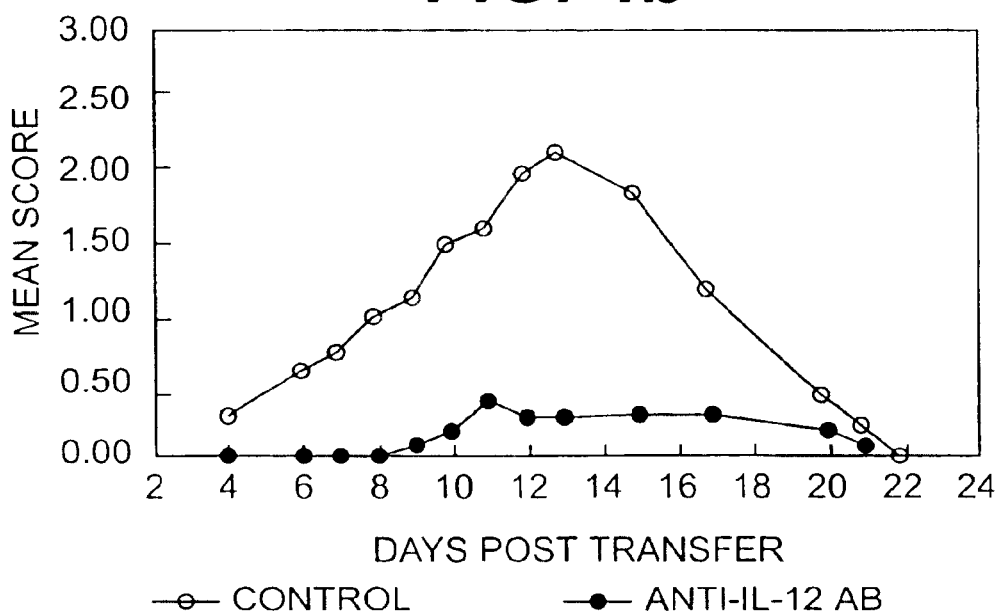

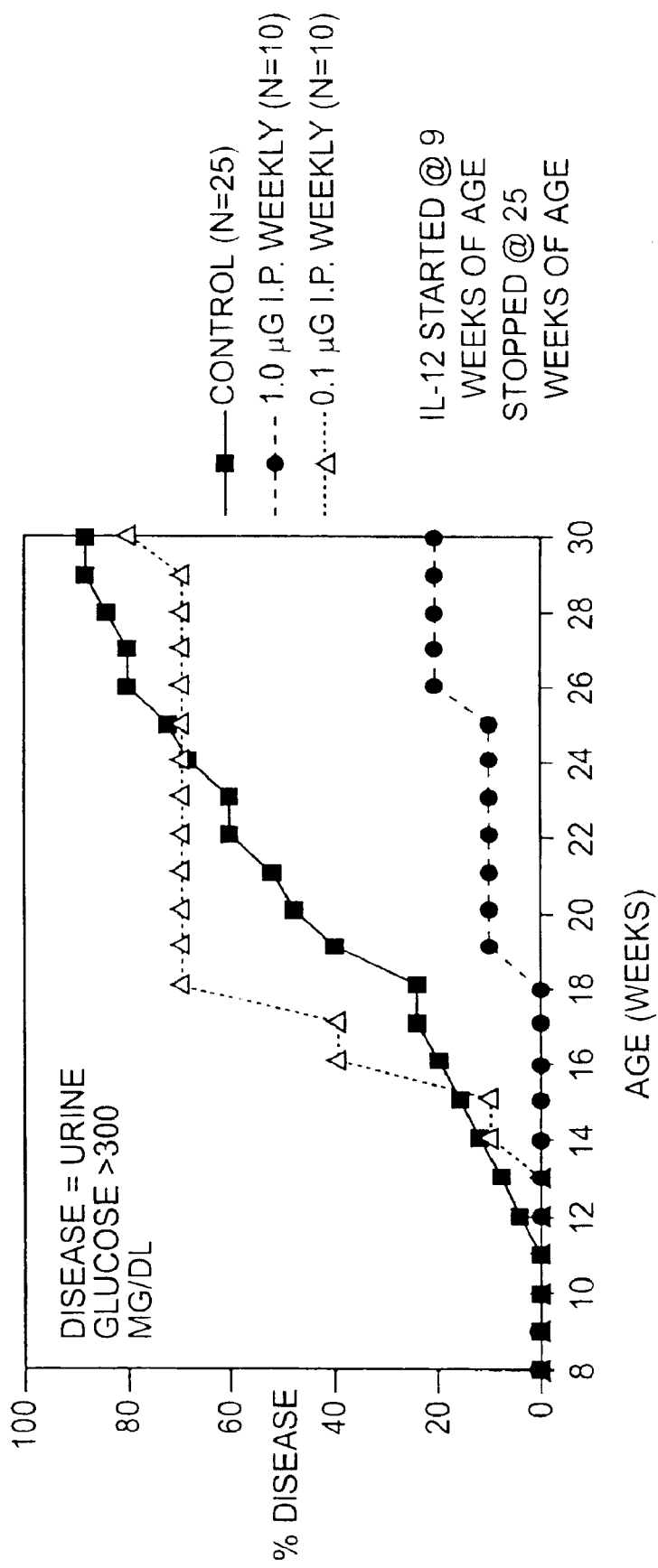

US 6,830,751 B1

USE OF IL-12 ANTAGONISTS IN THE TREATMENT OF RHEUMATOID ARTHRITIS

This application is a divisional of application Ser. No. 08/560,943, filed Nov. 20, 1995, now abandoned; which is a file-wrapper-continuation of application Ser. No. 08/212,629, filed Mar. 14, 1994, now abandoned; all of which are incorporated by reference herein.

BACKGROUND OF THE INVENTION

Gamma interferon (IFN-γ) and tumor necrosis factor-alpha (INF-α) have been implicated in the development, exacerbation and/or recurrence of numerous autoimmune conditions. For example, both IFN-γ and TNF-α have been associated with the course of multiple sclerosis [Choflon et al., Eur. Cytokine Netw. 3(6), 1992, pp. 523–531; Steinman, Scientific American, September 1993, pp. 107–114; Hofman et al., J. Exp. Med. 170, 1989, pp. 607–612; Panitch et al., Neurology, 37, 1987, pp. 1097–1102] and Type-I diabetes (insulin-dependent diabetes melitis, IDDM) [Castano et al., Annu. Rev. Immunol. 8, 1990, pp. 647–679; Campbell et al., J. Clin. Invest. 87, 1991, pp. 739–742]. While TNF-α has been found to promote development of rheumatoid arthritis [Feldmann et al., Progress in Growth Factor Research, 4, 1992, pp. 247–255], administration of IFN-γ has been linked to improvements in arthritic subjects [Veys et al., J. Rheumatology, 15(4), 1988, pp. 570–574]. Studies have also demonstrated the involvement of IFN-γ in the autoimmune diseases processes associated with systemic lupus erythematosus (SLE) [Funauchi et al., Tohoku J. Exp. Med., 164, 1991, pp. 259–267; Bankhurst, J. Rheumatology, 14(supp. 13), 1987, pp. 63–67], autoimmune thyroiditis [Tang et al., Eur. J. Immunol. 23, 1993, pp. 275–278], and autoimmune inflammatory eye disease (e.g., autoimmune uveoretinitis) [Charteris et al., Immunology 75, 1992, pp. 463–467]. Development of autoimmune pulmonary inflammation [Deguchi et al., Clin. Exp. Immunol. 85, 1991, pp. 392–395] and Guillain-Barre syndrome [Baron et al., Proc. Natl. Acad. Sci. USA 90, 1993, pp. 4414–4418] have also been tied to TNF-α activity.

Interleukin-12 (IL-12) is a heterodimeric cytokine which was originally identified as a factor which induces IFN-γ from T cells and natural killer cells as set forth in PCT/US91/06332, published Apr. 2, 1992. PCT/US91/06332 refers to IL-12 as Natural Killer Cell Stimulating Factor or NKSF. EP 433827, published Jun. 26, 1991 discloses IL-12 as a cytotoxic lymphocyte maturation factor (CLMF). IL-12 also stimulates natural killer cells in vitro by increasing their ability to lyse target cells at a level comparable to that obtained with IFN-α and IL-2, well-known activators of natural killer cells' cytotoxic activity. Additional in vitro activities of IL-12 which have been identified include induction of TNF-α; induction of T cell proliferation as a co-stimulant; suppression of IL-2 induced proliferation of natural killer blasts; suppression of IL-2 induced proliferation of T cell receptor-γδ-positive cells; promotion of Th1 T cell differentiation from progenitors; enhancement of Th1, but not Th2 proliferation; enhancement of T cell cytolytic activity; enhancement of cytotoxic lymphocyte generation; enhancement of natural killer and natural killer blast cytolytic activity; ex vivo enhancement of natural killer activity in peripheral blood mononuclear cells of IL-2-treated patients; induction of adhesion molecules on natural killer cells; induction of perforin and granzyme B mRNAs in natural killer blasts; induction of IL-2 receptor subunits (p55, p75) on natural killer cells; suppression of IgE synthesis by IFN-γ-dependent and independent mechanisms; modulation of T cell development in fetal thymic organ cultures; and synergy with kit ligand to promote growth of myeloid and B cell progenitors. The known in vivo activities of IL-12 include induction of IFN-γ; enhancement of natural killer cell activity in spleen, liver, lungs and peritoneal cavity; enhancement of generation of allo-specific cytotoxic lymphocytes; induction of extramedullary hematopoiesis in mouse spleen; reversible suppression of hematopoiesis in bone marrow; reversible induction of anemia, lymphopenia, and neutropenia in mice; suppression of anti-IgD induced IgE, IgG1, and IL4 expression; increased survival in SCID mice treated with *Toxoplasma gondii;* cure of leishmaniasis in susceptible strains of mice; decreased bioburden in cryptococcoses model; suppression of tumor growth; and promotion of immunity to tumor cells. IL-12 is also induced in vivo in the shwarzman reaction model of septic shock.

Although IL-12 can induce production of IFN-γ and TNF-α in vivo, the relationship of in vivo levels of IL-12 to autoimmune diseases which are affected by levels of IFN-γ and TNF-α has not been established. Furthermore, the effects of administration of IL-12 or antagonists of endogenous IL-12 (such as anti-IL-12 antibodies) on autoimmune diseases associated with induction of IFN-γ or TNF-α have not been examined.

SUMMARY OF THE INVENTION

The present invention provides methods of treating (e.g., curing, ameliorating, delaying or preventing onset of, preventing recurrence or relapse of) autoimmune conditions or diseases. In preferred embodiments, the condition is one promoted by an increase in levels of a cytokine selected from the group consisting of TNF-α or IFN-γ. Such conditions include, without limitation, those selected from the group consisting of multiple sclerosis, systemic lupus erythematosus, rheumatoid arthritis, autoimmune pulmonary inflammation, Guillain-Barre syndrome, autoimmune thyroiditis, insulin dependent diabetes melitis and autoimmune inflammatory eye disease. Multiple sclerosis and insulin-dependent diabetes melitis are particularly preferred conditions for treatment in accordance with the present invention as described herein.

In certain embodiments the method of treatment of the present invention comprises administering to a mammalian subject a therapeutically effective amount of an IL-12 antagonist, preferably an antibody or other species which is immunoreactive with IL-12. in certain preferred embodiments, the IL-12 antagonist is administered in a dose of about 0.05 to about 25 mg/kg, preferably of about 0.2 to about 2 mg/kg. The antagonists can also be administered in combination with a pharmaceutically acceptable carrier.

In other embodiments, the method of treatment of the present invention comprises administering to a mammalian subject a therapeutically effective amount of IL-12. In certain embodiments, the IL-12 may be administered in a dose of about 0.001 to about 1000 μg/kg, preferably about 0.01 to about 100 μg/kg. The IL-12 can also be administered in combination with a pharmaceutically acceptable carrier.

BRIEF DESCRIPTION OF THE FIGURES

FIG. 4 depicts graphs of data relating to the effects of in vivo administration of anti-IL-12 antibody on the adoptive transfer of EAE using PLP stimulated LNC. LNC from PLP immunized mice were cultured in vitro with antigen as described in materials and methods and 30×10⁶ cells transferred to naive mice. Anti-IL-12 antibody (sheep anti-mouse polyclonal antibody, 200 μg mouse) was administered by intraperitoneal injection starting on the day of cell transfer (closed circles). Control mice received an equivalent amount of sheep IgG (open circles). (a) Mean clinical score following administration of αIL-12 antibody everyother day from day 0 to day 6. (b) Mean clinical score following administration of αIL-12 antibody everyother day from day 0 to day 12. (n=5–7). See example 1.

FIGS. 5 and 6 present graphs of data relating to disease incidence in NOD mice upon administration of IL-12. See example 2.

DETAILED DESCRIPTION

Figure 1A:
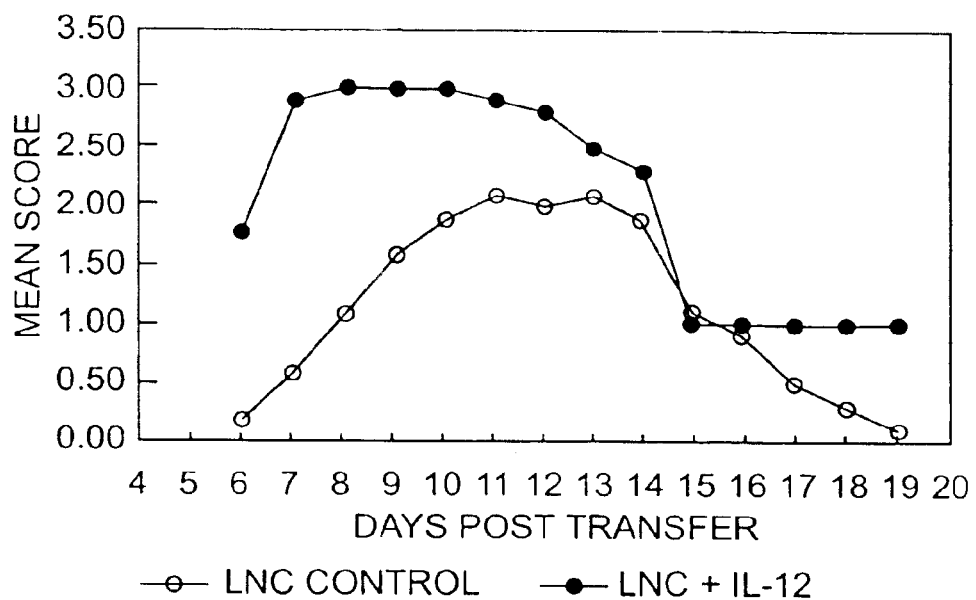
FIG. 1 presents graphs of data relating to the adoptive transfer of experimental allergic encephalomyelitis (EAE) using lymph node and spleen cells stimulated in vitro with PLP and rmIL-12. Spleens and Lymph nodes were harvested from mice 10 days after immunization with PLP and stimulated in vitro with antigen alone (open symbols) or antigen and 20ng/ml rmIL-12 (closed symbols) as described in materials and methods. Disease was transferred using 30×10⁶ cells. The results are presented as mean score for (a) lymph nodes (n=7) and (b) spleen cells (n=5). The data is representative of at least two separate experiments. See example 1.

The present invention provides methods for treating autoimmune conditions. "Autoimmune conditions" are those in which the subject's own immune system reacts against the subject's cells or tissues, resulting in damage to those cells or tissues. A particular autoimmune condition is "promoted by an increase in levels of a cytokine" when a increase in serum or tissue levels of such cytokine can cause or contribute to the development or recurrence of, or to the acceleration of the onset of, such autoimmune condition. Autoimmune conditions which are promoted by an increase in levels of IFN-γ and/or TNF-α include, without limitation, multiple sclerosis, systemic lupus erythematosus, rheumatoid arthritis, autoimmune pulmonary inflammation, Guillain-Barre syndrome, autoimmune thyroiditis, insulin dependent diabetes melitis and autoimmune inflammatory eye disease.

"IL-12 antagonists" include (1) species that will bind IL-12 or biologically active fragments thereof, and (2) species that will interfere with the binding of IL-12 to receptors or other binding proteins. Antagonists that bind IL-12 include, without limitation, antibodies (mono- or polyclonal) and fragments thereof (including $F_{ab}$ fragments), chimeric antibodies and fragments thereof, lectins, IL-12 receptors or fragments thereof, reactive peptides or fragments thereof, and organic small molecules designed to mimic the bioactivity of IL-12 receptors. Antagonists that interfere with IL-12 binding include, without limitation, chemically or genetically modified peptides of IL-12, subunits of IL-12 and fragments thereof, homopolymers of IL-12 subunits and fragments thereof, and organic small molecules designed to mimic the bioactivity of IL-12. Preferably, antagonists that interfere with IL-12 binding interfere with its binding to receptors which induce IFN-γ or TNF-α, without inducing the same level of such factors as would binding of IL-12 to the receptor.

IL-12 antagonists can be produced by methods well known to those skilled in the art. For example, monoclonal IL-12 antibodies can be produced by generation of antibody-producing hybridomas in accordance with known methods (see for example, Goding. 1983. Monoclonal antibodies: principles and paractice. Academic Press Inc., New York; Yokoyama. 1992. "Production of Monoclonal Antibodies" in Current Protocols in Immunology. Unit 2.5. Greene Publishing Assoc. and John Wiley & Sons). Polyclonal sera and antibodies to IL-12 can be produced by inoculation of a mammalian subject with IL-12 or fragments thereof in accordance with known methods. Chizzonite et al., J. Immunol. 148, 1992, p. 3117, describes the identification and isolation of an IL-12 receptor. Fragments of antibodies, receptors or other reactive peptides can be produced from the corresponding antibodies by cleavage of and collection of the desired fragments in accordance with known methods (see for example, Goding, supra; Andrew et al. 1992. "Fragmentation of Immunoglobulins" in Current Protocols in Immunology. Unit 2.8. Greene Publishing Assoc. and John Wiley & Sons). Chimerci antibodies may also be produced in accordance with known methods.

In methods of the present invention using IL-12, any form of IL-12 may be used, so long as that form of IL-12 is capable of treating the desired autoimmune condition. For example, IL-12 may be in the form of the heterodimer comprised of a 40 kD subunit disulfide-bonded to a 35 kD subunit. When IL-12 is a heterodimer, the 40 kD subunit has substantial homology to the 40 kD subunit of human IL-12 as set forth in PCT/US91/06332 and is disulfide bonded to a 35 kD subunit having substantial homology to the 35 kD subunit of human IL-12 as set forth in that same PCT publication. "Substantial homology" means greater than 75% homology at the amino acid level, while retaining the ability to treat the desired autoimmune condition in a mammalian subject. Another form of IL-12 which may be used in the present invention is an IL-12 subunit capable of treating the desired autoimmune condition in a mammalian subject. Such an IL-12 40 kD subunit has substantial homology to the human IL-12 40 kD subunit disclosed in PCT/US91/06332, and such an IL-12 35 kD subunit has substantial homology to the human IL-12 35 kD subunit disclosed in such PCT publication. Fragments of the IL-12 subunits that retain IL-12 biological activity are also be useful to treat autoimmune conditions in mammalian subjects, in accordance with the present invention.

For use in the present invention, it is preferable to produce IL-12 recombinantly, through expression of DNA sequences encoding one or both of the IL-12 subunits in a suitable transformed host cell. For example, using known methods the DNA sequences encoding human IL-12 set forth in PCT/US91/06332 may be linked to an expression vector such as pED (Kaufman et al., Nucleic Acids Res. 19, 4484–4490(1991)). In such an expression vector, sequences which optimize translation such as CCACC (Kozak, M., Nucleic Acids Res. 12, 857–871 (1984)) may be added 5' to the initiation codon using known methods. The expression vector containing the IL-12 subunits may then be transformed into a host cell, and protein expression may be induced and maximized, to produce heterodimeric human IL-12. For production of heterodimeric IL-12, the DNA sequences encoding the IL-12 subunits may be present on different expression plasmids or present in tandem on a single expression plasmid.

When a subunit or fragment of IL-12 is used to practice the present invention, it may also be produced recombinantly using known methods. For example, the DNA sequence encoding the human IL-12 40 kD subunit set forth in PCT/US91/06332 may be linked to an expression vector, transformed into a host cell, and expression induced and maximized to produce the human IL-12 40 kD subunit. Similarly, the DNA sequences encoding the human IL-12 35 kD subunit as set forth in the PCT publication may be linked to an expression vector, transformed into a host cell, and expression induced and maximized to produce the corresponding protein. Of course, degenerate DNA sequences encoding the IL-12 subunits may also be employed to produce IL-12 for use in the present invention, as can DNA sequences encoding allelic variants of the IL-12 subunits. Chemically or genetically modified forms of IL-12 and its subunits can also be made in accordance with the methods disclosed in the PCT publication.

Any suitable expression vector may be employed to produce IL-12 for use in the present invention. For mammalian expression, numerous expression vectors are known in addition to the pED vector mentioned above, such as pEF-BOS (Mizushima et al., Nucleic Acids Res. 18, 5322 (1990)); pXM, pJL3 and pJL4 (Gough et al., EMBO J. 4, 645–653 (1985)); and pMT2 (derived from pMT2-VWF, A.T.C.C. #67122; see PCT/US87/00033). Suitable expression vectors for use in yeast, insect, and bacterial cells are also known. Construction and use of such expression vectors is well within the level of skill in the art.

Suitable host cells for recombinant production of IL-12 useful in the present invention include, for example, mammalian cells such as Chinese hamster ovary (CHO) cells, monkey COS cells, mouse 3T3 cells, mouse L cells, myeloma cells such as NSO (Galfre and Milstein, Methods in Enzymology 73, 346 (1981)), baby hamster kidney cells, and the like. IL-12 may also be produced by transformation of yeast, insect, and bacterial cells with DNA sequences encoding the IL-12 subunits, induction and amplification of protein expression, using known methods.

Recombinantly produced IL-12 can be purified from culture medium or cell extracts by conventional purification techniques. Culture medium or cell extracts containing IL-12 may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. The purification of IL-12 from culture supernatant may also include one or more column steps over such affinity resins as lectin-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify IL-12 for use in the present methods and compositions. Some or all of the foregoing purification steps, in various combinations, can be employed to provide a substantially homogeneous isolated recombinant protein. Purification of IL-12 subunits or fragments for use in the present invention may differ from the optimal protocol for purification of the heterodimeric protein.

Preferably, when human IL-12 is produced recombinantly as set forth above, it may be purified by the following method. The cells in which the human IL-12 has been made may be removed from the conditioned medium by filtration, and the conditioned medium is loaded onto Q-Sepharose FastFlow™ (available from Pharmacia) or an equivalent anion exchange medium, which has been equilibrated in 10–30 mM Tris-HCl, pH 7.8–8.3. The column is then washed extensively with the same buffer followed by a wash with 30–45 mM histidine, pH 5.1–5.8, followed by a wash with the original equilibration buffer. The recombinant human IL-12 is eluted from the column with a buffer containing 20–50 mM Tris-HCl, pH 7.8–8.5, and 0.15 to 0.50 M NaCl. The eluted material is loaded onto CM-Sepharose FastFlow™ (available from Pharmacia) or equivalent cation exchange medium which has been equilibrated in 20–50 mM MES, pH 5.7–6.4, and washed extensively with the same buffer. The column is washed with a buffer containing 20–40 mM sodium phosphate, pH 6.8–7.5 and 0.2–0.5 M NaCl. The eluted material is concentrated using an Amicon™ S1Y30 or equivalent spiral cartridge membrane which has been washed and equilibrated in the elution buffer used in the CM-Seplarose FastFlow™ column. The material is concentrated to approximately 5% of the column volume of the final chromatographic step, which is size exclusion using S200 Sephacryl™ (available from Pharmacia) or an equivalent size exclusion resin. The size exclusion column is equilibrated and eluted with phosphate buffered saline, pH 7.2–7, and the recombinant human IL-12 peak is collected and filtered for use in the method of the invention. Those of skill in the art of protein purification may use alternative purification methods to obtain recombinantly-produced human IL-12 for use in the method of the invention.

IL-12 may be purified from culture medium or extracts of cells which naturally produce the protein and used in the present invention. Exemplary purification schemes for naturally produced IL-12 are set forth in PCT/US91/06332 and in EP 433827.

Pharmaceutical compositions containing an IL-12 antagonist or IL-12 which are useful in practicing the methods of the present invention may also contain pharmaceutically acceptable carriers, diluents, fillers, salts, buffers, stabilizers and/or other materials well-known in the art. The term "pharmaceutically acceptable" means a material that does not interfere with the effectiveness of the biological activity of the active ingredient(s) and that is not toxic to the host to which it is administered. The characteristics of the carrier or other material will depend on the route of administration.

It is currently contemplated that the various pharmaceutical compositions should contain about 0.1 micrograms to about 1 milligram per milliliter of the IL-12 antagonist or IL-12.

Administration can be carried out in a variety of conventional ways. Intraperitoneal injection is the preferred method of administration of the IL-12 antagonist or IL-12. Intravenous, cutaneous or sub-cutaneous injection may also be employed. For injection, IL-12 antagonist or IL-12 will preferably be administered in the form of pyrogen-free, parenterally acceptable aqueous solutions. The preparation of such parenterally acceptable protein solutions, having due regard to pH, isotonicity, stability and the like, is within the skill of the art.

The amount of IL-12 antagonist or IL-12 used for treatment will depend upon the severity of the condition, the route of administration, the reactivity of the IL-12 antagonist with IL-12 or the activity of the IL-12, and ultimately will be decided by the treatment provider. In practicing the methods of treatment of this invention, a therapeutically effective amount of an IL-12 antagonist or IL-12 is administered. The term "therapeutically effective amount" means the total amount of each active component of the method or composition that is sufficient to show a meaningful patient benefit (e.g., curing, ameliorating, delaying or preventing onset of, preventing recurrence or relapse of). One common technique to determine a therapeutically effective amount for a given patient is to administer escalating doses periodically until a meaningful patient benefit is observed by the treatment provider. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of an IL-12 antagonist in this invention is contemplated to be in the range of about 0.05 mg/kg to about 25 mg/kg. A therapeutically effective dose of IL-12 in this invention is contemplated to be in the range of about 0.001 to about 1000 $\mu$g/kg. The number of administrations may vary, depending on the individual patient and the severity of the autoimmune condition.

The IL-12 antagonist or IL-12 used in practicing the present invention may be administered alone or combined with other therapies for autoimmune conditions, such as steroidal or other anti-inflammatory therapies and administration of other cytokines.

The methods of the present invention are further described in the following examples, which are intended to illustrate the invention without limiting its scope.

EXAMPLE 1

Experimental allergic encephalomyelitis (EAE) is a T cell mediated autoimmune disease of the central nervous system (CNS). Disease can be induced in susceptible strains of mice by immunization with CNS myelin antigens or alternatively, disease can be passively transferred to susceptible mice using antigen stimulated CD4+ T cells [Pettinelli, J. Immunol. 127, 1981, p. 1420]. EAE is widely recognized as an acceptable animal model for multiple sclerosis in primates [Alvord et al. (eds.) 1984. Experimental allergic encephalomyelitis—A useful model for multiple sclerosis. Alan R. Liss, New York]. The effects of administration of an IL-12 antagonist on induction of EAE following the adoptive transfer of lymphocytes from immunized mice restimulated in vitro with a synthetic peptide of myelin proteolipid protein (PLP).

Adoptive Transfer of PLP Sensitized LNC

Female SJL/J mice (7–10 wks) were purchased from The Jackson Laboratory, housed 5 to a cage and fed standard rodent chow diet with water ad libitum. Mice were immunized in two sites on the flank with 150 $\mu$g of mouse PLP peptide comprising residues 139–151 (provided by G Brown, Genetics Institute). PLP was administered in $^{200}$ $\mu$l of Complete Freunds adjuvant containing 2 mg/ml *Mycobacteria Tuberculosis* H37RA (Difco). On the day of immunization mice were injected intravenously with $0.75 \times 10^{10}$ *Bordatella pertussis* bacilli (Massachusetts Public Health Laboratories, Boston, Mass.). Ten days after immunization, spleens and lymph nodes (popliteal, axillary and brachial) were harvested and the cells resuspended in RPMI-1640 containing 10% FBS (Hyclone), $5 \times 10^{-5}$ M 2-Mercaptoethanol, 100 $\mu$g/ml streptomycin and 100 U/ml penicillin. PLP was added to the cultures at 2 $\mu$g/ml. After 96 hours, the cells were harvested, washed twice and $30 \times 10^{\ne}$ cells (either LNC or spleen) injected i.p. into naive SJL/J mice.

Clinical Evaluation of Disease

Mice were observed for clinical signs of EAE and scored on a scale of 0 to 3 as follows:

0.5—Distal limp tail
1.0—Complete limp tail
1.5—Limp tail and hind limb weakness (unsteady gait)
2.0—Partial hind limb paralysis
3.0—Complete bilateral hind limb paralysis In Vitro Administration of IL-12 Prior to Cell Transfer Recombinant murine IL-12 (20 ng/ml, rmIL-12, Genetics Institute) was added to the in vitro cultures of lymph node or spleen cells with antigen prior to cell transfer. After 96 hours the cells were washed twice and $30 \times 10^6$ cell transferred to naive SJL/J mice to determine the effects of IL-12 on the subsequent course of disease.

In separate experiments, LNC were cultured with either antigen alone, antigen plus IL-12 (20 ng/ml) or antigen plus IL-12 plus a neutralizing antibody to IFN-$\gamma$ (5 $\mu$g/ml from Endogen). At the end of the culture period supernatants were collected (pooled from three flasks) and IFN-$\gamma$ and TNF-$\alpha$ measured by ELISA (from Genzyme). $30 \times 10^6$ cells from each group were transferred to naive mice which were monitored for signs of disease.

In vivo Administration of IL-12 and Anti-IL-12 Antibody Following the Transfer of PLP Stimulated LNC rmIL-12 (0.3 $\mu$g/mouse, 200 $\mu$l i.p.) was administered to mice following the transfer of either $30 \times 10^6$ or $10 \times 10^6$ PLP stimulated LNC. IL-12 was administered on days 0, 1 and 2 following cell transfer. Control mice received an equal volume of vehicle alone. To determine if IL-12 is involved in the induction of disease following the transfer of PLP stimulated LNC, mice were treated with 200 $\mu$g of a sheep polyclonal antibody against murine IL-12 (200 $\mu$l i.p.) on alternate days for either 6 or 12 days in total following cell transfer and the mice monitored for signs of disease. Control mice received and equal amount of sheep IgG. The mice were monitored.

Effect of rmIL-12 on Restimulation of PLP Primed T Cells in vitro

LNC from mice immunized with PLP as described in methods were stimulated in vitro with antigen in the absence or presence of rmIL-12 (20 ng/ml) for 96 hours after which time they were tested for their ability to transfer disease to naive SJL/J mice. Mice receiving LNC stimulated in vitro with PLP alone developed clinical signs of disease between days 6 and 8. All control mice reached scores of 2 or greater (7/7) with 4 out of 7 mice progressing to complete hind limb paralysis which lasted between 1 and 4 days (FIG. 1a). All the control mice had recovered by day 19. In contrast mice receiving cells cultured in vitro with PLP and IL-12 developed severe EAE with rapid onset of clinical signs (FIG. 1a). By day 6, 4 out 7 mice had clinical scores of 2 or greater and all mice went on to develop full hind limb paralysis by day 8. In this particular experiment 5 out of 7 mice failed to recover from the paralysis.

Figure 1B:
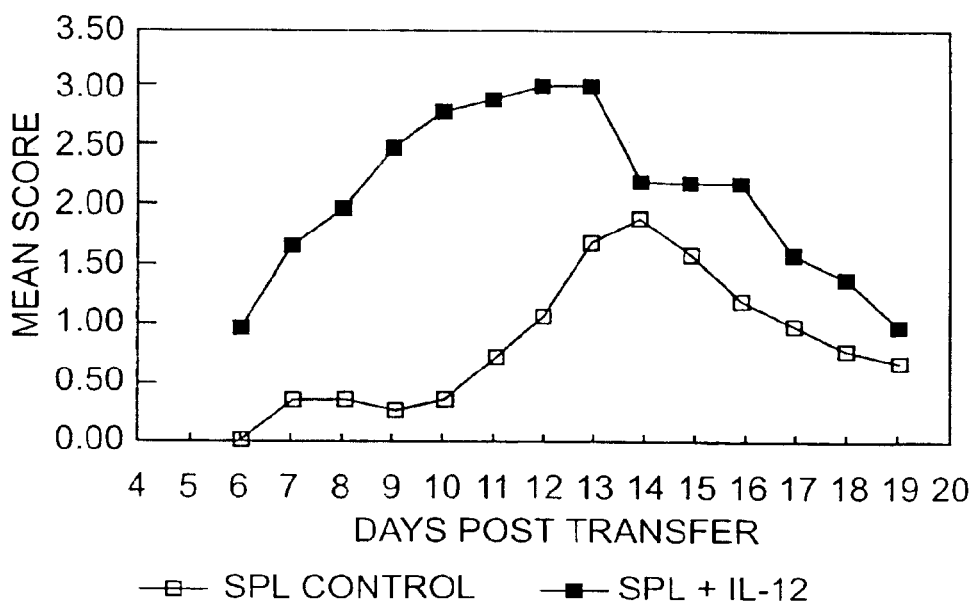

Spleen cells from PLP immunized mice stimulated in vitro with antigen for 96 hours in the absence or presence of rmIL-12 (20 ng/ml) were also examined to determine whether they could transfer disease to naive SJL/J mice. The severity of disease following the adoptive transfer of 30×10$^6$ PLP stimulated spleen cells was mild compared to that induced by an equivalent number of PLP stimulated LNC, with only 2 out of 5 mice developing complete hind limb paralysis and the remaining 3 mice displaying only mild signs of disease (FIG. 1b). Similar to the results observed with LNC, the addition of rmIL-12 (20 ng/ml) to the in vitro culture of spleen cells prior to transfer exacerbated subsequent disease (FIG. 1b). Mice receiving spleen cells stimulated with PLP and rmIL-12 developed clinical signs of disease by day 6 and all progressed to full hind limb paralysis by day 12. The mean duration of paralysis in these mice was 5.4 days (range 2–8 days).

Cytokine Production Following in vitro Stimulation of LNC with PLP and IL12

Figure 2A:
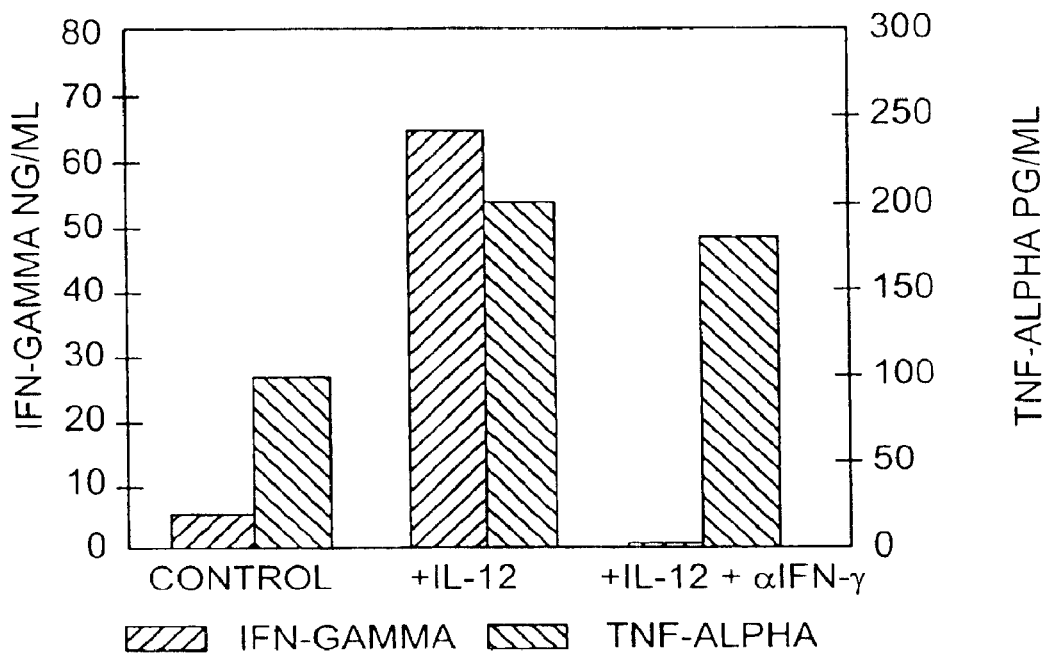
FIG. 2 presents graphs of data relating to IFN-γ and TNF-α production from LNC stimulated in vitro with PLP and IL-12. LNC (2.5×10⁶/ml) from PLP immunized mice were cultured with PLP alone, PLP and rmIL-12 (20 ng/ml) or PLP, rmIL-12 and anti-IFN-γ (5 μg/ml) for 96 hours prior to cell transfer with 30×10⁶ cells. (a) IFN-γ and TNF-α measured by ELISA in the supernatants of pooled cultures. (b) Mean disease score after the transfer of stimulated lymph node cells. n=3 for PLP alone and PLP+IL-12 and n=4 for PLP+IL-12+anti-IFN-γ. See example 1.
Figure 2B:
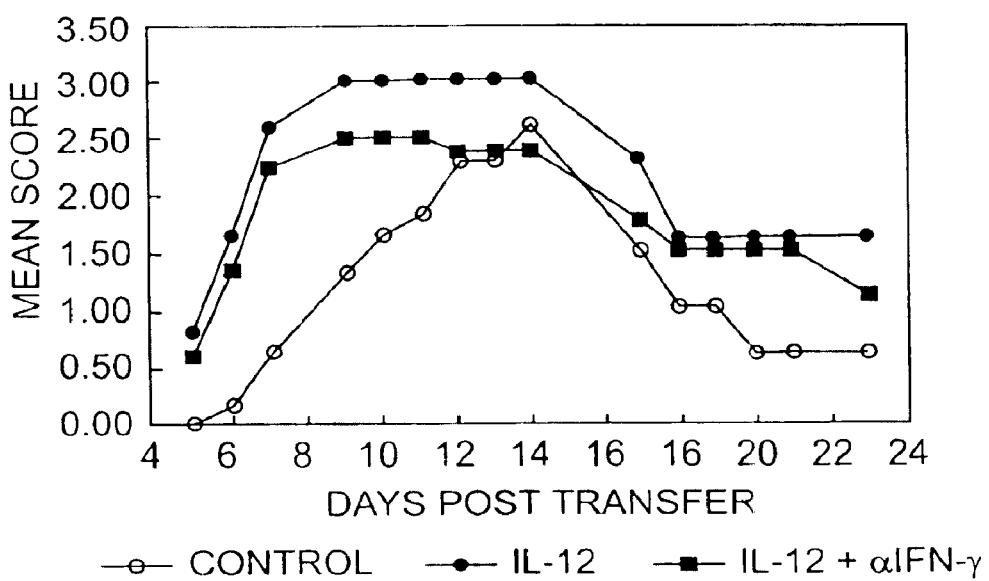

To determine the effects of IL-12 on cytokine production during the in vitro stimulation with antigen, LNC from PLP primed mice were cultured with either PLP alone, PLP and IL-12 (20 ng/ml) or PLP, IL-12 and a neutralizing anti-IFN-γ antibody. At the end of the in vitro culture, IFN-γ and TNF-α in the supernatant were measured by ELISA and the cells tested for their ability to transfer disease to naive mice. The addition of IL-12 during the in vitro stimulation of LNC with PLP resulted in a greater than 10 fold increase in IFN-γ (5.2 ng/ml control and 64 ng/ml IL-12) and a two fold increase in TNF-α in the cell culture supernatant (FIG. 2a). The addition of a neutralizing antibody to IFN-65 during the culture of LNC with antigen and IL-12 completely blocked IFN-γ detection, but had no effect on the increase in TNF-α in the supernatants which remained approximately two fold higher relative to controls (100 pg/ml controls compared to 180 pg/ml with αIFN-γ antibody). Furthermore, transfer of the cells stimulated in vitro with PLP and IL-12 in the presence of a neutralizing antibody to IFN-γ were still capable of inducing severe disease with the same kinetics and duration to that seen following the transfer of cells stimulated with PLP and IL-12 alone (FIG. 2b).

The Effect of in vivo Administration of IL-12 on Disease Progression

Figure 3A:
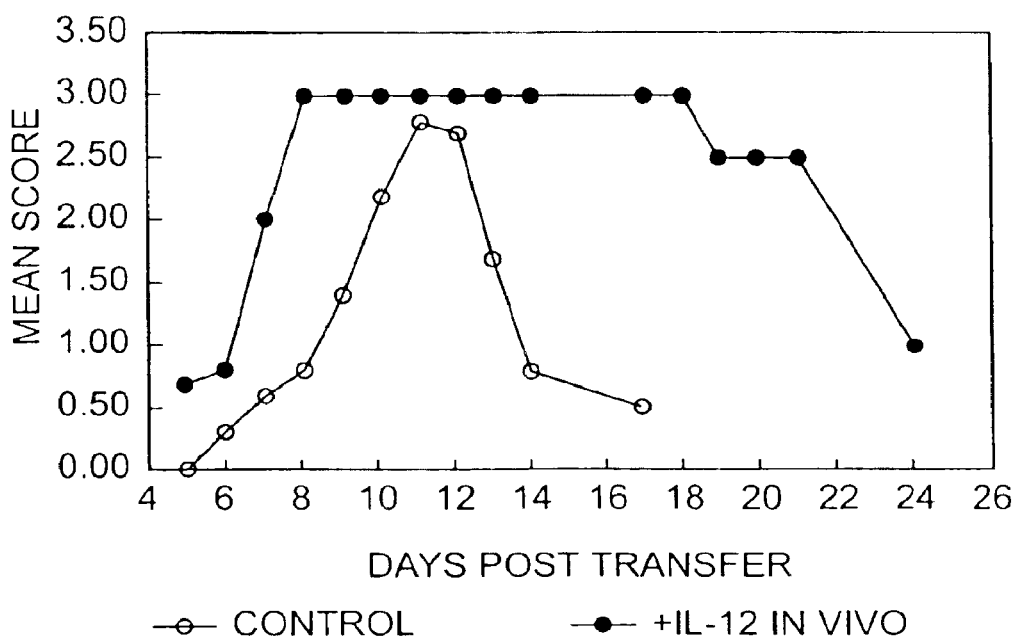
FIG. 3a is representative of three separate experiments. See example 1.

Following the transfer of 30×10$^6$ PLP stimulated LNC mice were administered rmIL-12 (0.3 μg/mouse) or saline for 3 days and the effects on the subsequent course of disease monitored. The onset and progression of disease in the controls was similar to that described above with clinical signs evident between days 6–8 after the transfer of LNC with 80% of the mice progressing to full bilateral hind limb paralysis. Peak disease in the control mice lasted approximately 3 days after which time the mice spontaneously recovered (FIG. 3a). Administration of rmIL-12 (0.3 μg/mouse) for 3 days after the transfer of an equivalent number of primed LNC from the same in vitro cultures dramatically altered the course of disease. Although the time of onset of symptoms was only slightly earlier in the IL-12 treated mice (day 5), the subsequent progression to peak disease was accelerated with all mice displaying full hind limb paralysis by day 8. The duration of paralysis was also significantly prolonged lasting up to 14 days (range 11–14). Several mice treated with rmIL-12 that developed prolonged paralysis which persisted after the controls had fully recovered were sacrificed.

Figure 3B:
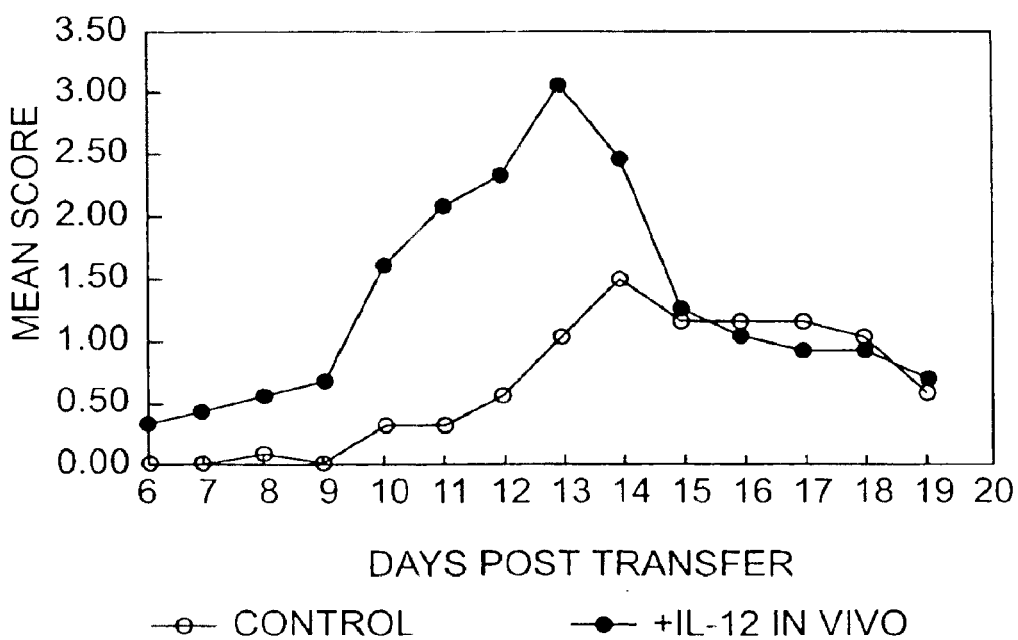
FIG. 3 depicts graphs of data relating to the effects of In vivo administration of IL-12 on the adoptive transfer of EAE using PLP stimulated LNC. LNC from PLP immunized mice were cultured in vitro with antigen as described in materials and methods and transferred to naive mice. rmIL-12 (0.3 μg/mouse) was administered on days 0, 1 and 2 after cell transfer (closed circles) and mice monitored for signs of disease. Control mice received and equal volume of saline (open circles). (a) Mean clinical score following the transfer of 30×10⁶ LNC cells (n=5). (b) Mean clinical score following the transfer of 10×10⁶ LNC (n=4).

In a separate experiment, the effects of in vivo administration of rmIL-12 on disease severity was examined following the transfer of a suboptimal number of LNC (10×10$^6$ cells). Control mice receiving this lower number of LNC developed mild disease (FIG. 3b) with 1 out of 4 animals progressing to full hind limb paralysis and only minimal disease in the remaining 3 controls. In contrast, mice treated with rmIL-12 in vivo following the transfer of 10×10$^6$ LNC cells developed full clinical symptoms of disease with all mice scoring 2 or greater and 3 out of 4 mice progressing to full hind limb paralysis. The effects of rmIL-12 were also apparent after the transfer of as few as 5×10$^6$ LNC cells with 3 out of 5 mice reaching a score of 1. At this cell number controls showed no signs of disease (data not shown).

The effects of Anti-IL-12 Antibody Administration on the Course of Disease

To determine if endogenous IL-12 plays an essential role in disease transfer, mice were treated with 200 μg of a sheep polyclonal antibody to murine IL-12 every other day for either 6 or 12 days following the transfer of 30×10$^6$ PLP stimulated LNC cells. Controls received an equal amount of sheep IgG. The onset of clinical signs in the Sheep IgG treated controls was similar to that seen in untreated mice receiving PLP stimulated LNC (day 6–7, FIG. 4a). All control mice developed signs of disease graded 2 or greater (70% developed full paralysis). Administration of the ant-IL-12 antibody during the first 6 days after transfer did reduce the severity of disease, however, the onset of clinical signs was delayed by approximately 7 days. These mice subsequently went on to develop disease with all mice reaching a score of 2 or greater (80% developed full paralysis) with a similar time course of recovery to control animals. To determine if this delay of disease transfer could be sustained by a longer administration of anti-IL-12 antibody, we treated mice for 12 days following adoptive transfer of PLP primed LNC. Mice treated with anti-EL-12 antibody every other day for 12 days after the transfer of PLP stimulated LNC not only showed a more sustained delay in the kinetics of disease onset but also experienced dramatically reduced clinical disease with only 2 out of 5 mice developing mild signs of disease (FIG. 4b).

EXAMPLE 2

NOD/LtJ mice (Jackson Laboratories) were treated with IL-12 to gauge the effect of the cytokine on an accepted animal model of insulin-dependent diabetes melitis (IDDM) [Kutani et al., Adv. Immunol. 51, 1992, p. 285]. Female NOD mice spontaneously develop an IDDM-like disease with destruction of the Beta cells in the pancreas and spilling of glucose into the urine beginning around 12–14 weeks of age. In the inventor's animal facility, female NOD mice show a disease incidence of approximately 88% by 30 weeks of age.

Female NOD mice were treated with two different protocols. In Treatment A, mice were given 10, 1 or 0.1 μg (0.5, 0.05 or 0.005 mg/kg) murine IL-12 (mIL-12) i.p. three times a week for two weeks beginning at 9–11 weeks of age. In Treatment B, mice were given 1 or 0.1 μg mIL-12 i.p. once a week beginning at 9 weeks of age and were continued on treatment until 25 weeks of age.

Figure 5:
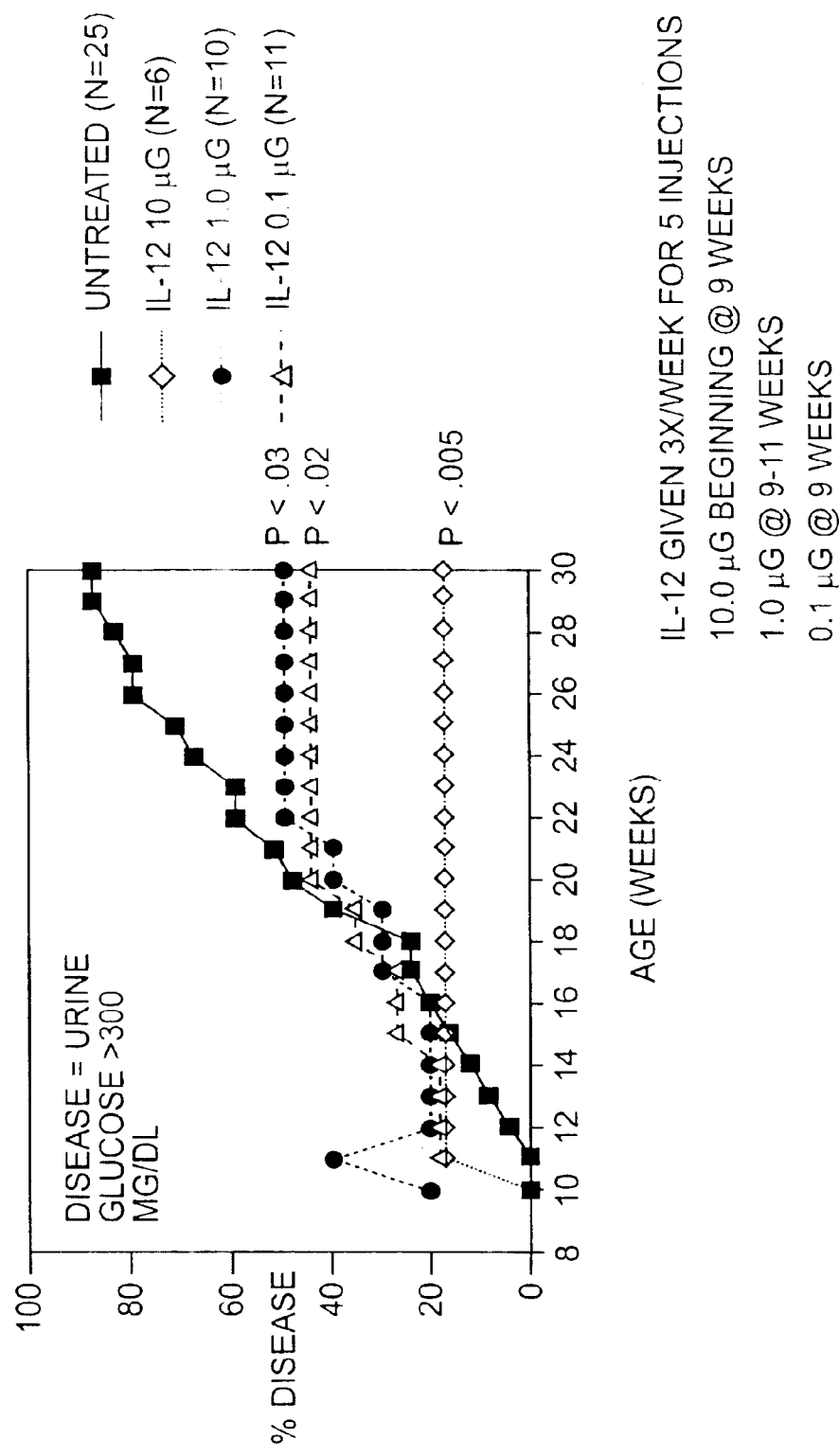

Mice under Treatment A receiving all three doses showed statistically significant decreases of disease incidence, with the 10 μg dose being most effective (17% disease incidence) (see Table 1 and FIG. 5). Mice under Treatment B receiving 1 μg weekly showed a large decrease in disease incidence (20%), while mice receiving 0.1 μg did not show a measurable change in disease incidence (80%) (see Table 1 and FIG. 6).

TABLE 1

INCIDENCE OF DIABETES IN IL-12 TREATED NOD MICE

| | | IL-12 3X/week 2 weeks* | | | IL-12 weekly† | |
|---|---|---|---|---|---|---|
| age | unRx | 10 μg | 1 μg | 0.1 μg | 1 μg | 0.1 μg |
| 8 | | | | | 0/10 | 0/10 |
| 9 | | | | | 0/10 | 0/10 |
| 10 | 0/10 | 0/6 | 1/5 | 0/11 | 0/10 | 0/10 |
| 11 | 0/20 | 1/6 | 2/5 | 2/11 | 0/10 | 0/10 |
| 12 | 1/25 | 1/6 | 2/10 | 2/11 | 0/10 | 0/10 |
| 13 | 2/25 | 1/6 | 2/10 | 2/11 | 0/10 | 0/10 |
| 14 | 3/25 | 2/6 | 2/10 | 2/11 | 0/10 | 1/10 |
| 15 | 4/25 | 1/6 | 2/10 | 3/11 | 0/10 | 1/10 |
| 16 | 5/25 | 1/6 | 2/10 | 3/11 | 0/10 | 4/10 |
| 17 | 6/25 | 1/6 | 3/10 | 3/11 | 0/10 | 4/10 |
| 18 | 6/25 | 1/6 | 3/10 | 4/11 | 0/10 | 7/10 |
| 19 | 9/25 | 1/6 | 3/10 | 4/11 | 1/10 | 7/10 |
| 20 | 12/25 | 1/6 | 4/10 | 5/11 | 1/10 | 7/10 |
| 21 | 12/25 | 1/6 | 4/10 | 5/11 | 1/10 | 7/10 |
| 22 | 14/25 | 1/6 | 5/10 | 5/11 | 1/10 | 7/10 |
| 23 | 15/25 | 1/6 | 5/10 | 5/11 | 1/10 | 7/10 |
| 24 | 16/25 | 1/6 | 5/10 | 5/11 | 1/10 | 7/10 |
| 25 | 18/25 | 1/6 | 5/10 | 5/11 | 1/10 | 7/10 |
| 26 | 20/25 | 1/6 | 5/10 | 5/11 | 2/10 | 7/10 |
| 27 | 20/25 | 1/6 | 5/10 | 5/11 | 2/10 | 7/10 |
| 28 | 21/25 | 1/6 | 5/10 | 5/11 | 2/10 | 7/10 |
| 29 | 22/25 | 1/6 | 5/10 | 5/11 | 2/10 | 7/10 |
| 30 | 22/25 | 1/6 | 5/10 | 5/11 | 2/10 | 8/10 |

*treatment started at 9–10 weeks of age and continued for two weeks
†treatment started at 9 weeks of age and continued for 15 weeks All patent and literature references cited herein are incorporated by reference as if fully set forth.

What is claimed is:

1. A method for treating rheumatoid arthritis in a human subject, said method comprising administering to said subject a therapeutically effective amount of an IL-12 antagonist that binds with IL-12, wherein said antagonist is chosen from a group consisting of an antibody immunoreactive with IL-12 and an antibody fragment immunoreactive with IL-12.

2. The method of claim 1, wherein said antagonist is administered in combination with a pharmaceutically acceptable carrier.

3. The method of claim 1, wherein said antagonist is an antibody immunoreactive with IL-12.

4. The method of claim 1, wherein said antagonist is an antibody fragment is immunoreactive with IL-12.

5. The method of claim 1, wherein the antibody is a monoclonal antibody.

6. The method of claim 1, wherein the antibody binds to a heterodimer comprised of a 40 kD subunit and an 35 kD subunit of IL-12.

7. The method of claim 1, wherein said antagonist is administered in a dose of from about 0.05 to about 25 mg/kg.

8. The method of claim 1, wherein said antagonist is administered in a dose of from about 0.2 to about 2 mg/kg.

9. The method of claim 1, wherein said antagonist is administered intravenously.

10. The method of claim 1, wherein said antagonist is administered subcutaneously.

11. The method of claim 1, wherein said antagonist is administered cutaneously.

12. The method of claim 1, wherein said antagonist is administered in combination with other therapies for autoimmune conditions.

13. The method of claim 12, wherein said therapies comprise steroidal or other anti-inflammatory therapies.

* * * * *

UNITED STATES PATENT AND TRADEMARK OFFICE
CERTIFICATE OF CORRECTION

PATENT NO.    : 6,830,751 B1
DATED         : December 14, 2004
INVENTOR(S)   : John Leonard et al.

It is certified that error appears in the above-identified patent and that said Letters Patent is hereby corrected as shown below:

Column 12,
Line 15, "fragment is immunoreactive" should read -- fragment immunoreactive --.

Signed and Sealed this

First Day of March, 2005

JON W. DUDAS
*Director of the United States Patent and Trademark Office*